(12) United States Patent
Kang et al.

(10) Patent No.: US 8,053,219 B2
(45) Date of Patent: Nov. 8, 2011

(54) METHOD FOR PRODUCTION OF HIGH PURITY POLYHYDROXYALKANONATE (PHAS)

(75) Inventors: Shih-Hsu Kang, Taoyuan Hsien (TW); Yi-Ming Sun, Taoyuan Hsien (TW); Chih-Ching Chien, Taoyuan Hsien (TW); Shih-Chen Tang, Taoyuan Hsien (TW); Chang-Chieh Chen, Taoyuan Hsien (TW)

(73) Assignee: Yuan Ze University, Taoyuan Hsien (TW)

( * ) Notice: Subject to any disclaimer, the term of this patent is extended or adjusted under 35 U.S.C. 154(b) by 818 days.

(21) Appl. No.: 12/122,551

(22) Filed: May 16, 2008

(65) Prior Publication Data

US 2008/0299627 A1  Dec. 4, 2008

(30) Foreign Application Priority Data

May 29, 2007 (TW) ................................ 96119112 A

(51) Int. Cl.
*C12P 7/62* (2006.01)
*C07C 69/66* (2006.01)
(52) U.S. Cl. ........................................ 435/135; 560/179
(58) Field of Classification Search .................... 435/135
See application file for complete search history.

(56) References Cited

U.S. PATENT DOCUMENTS

| 6,083,729 A | * | 7/2000 | Martin et al. | ................. 435/135 |
| 6,709,849 B2 | * | 3/2004 | Cheung | ..................... 435/173.1 |

* cited by examiner

*Primary Examiner* — Herbert J Lilling
(74) *Attorney, Agent, or Firm* — WPAT, P.C.; Anthony King

(57) ABSTRACT

The present invention relates to a method of producing polyhydroxyalkanoates (PHAs) using *Bacillus* sp. with succinate as a carbon source. The PHAs comprise more than 95% of poly(3-hydroxyvalerate-co-4-hydroxyvalerate) (P3HV-co-P4HV).

3 Claims, 6 Drawing Sheets

METHOD FOR PRODUCTION OF HIGH PURITY POLYHYDROXYALKANONATE (PHAS)

BACKGROUND OF THE INVENTION

1. Field of the Invention

The present invention relates to a polyhydroxyalkanoates (PHAs) production method. More than 95% of the PHAs are comprised of poly(3-hydroxyvalerate-co-4-hydroxyvalerate) (P3HV-co-P4HV). PHAs are produced by *Bacillus* sp., which is cultivated under the condition with unbalanced nutrients and supplemented with a carbon source of succinate.

2. The Prior Arts

Plastic materials produced from traditional petrochemical industry are light weight and durable, and are convenient for daily use. However, they increasingly contribute to serious environmental problems such as pollution because of their persistence. Additionally, the limited availability and high price of crude oil make it a very expensive starting material for PHA production. Therefore, the development of a sustainable substitute source for plastic production is urgently needed. Additionally, this new family of plastic will be biodegradable. Currently there are several types of biodegradable materials:

(1) Photodegradable Plastics

There have been numerous studies done in photodegradable plastics than in other degradable plastics. These products are created by introducing photoactive additives into copolymers which can be degraded when exposed to ultraviolet light. However, secondary pollution can be caused due to incomplete degradation of these plastics.

(2) Compostable Plastics

These plastics are made from natural resources like corn protein or plant starch added in plastic materials. However, they have poor resistance to water and heat rendering their daily use impractical.

(3) Chemical Synthesized Degradable Plastics

These products are synthesized from direct polymerization techniques, using polylactides, that are prepared by direct polycondensation of lactic acid. Polylactides are biodegradable and biocompatible but their molecular weights are low, and production costs are higher than those of the petrochemical materials.

(4) Polyhydroxyalkanotes (PHAs)

PHAs are polyesters produced by microorganisms. Hydroxyalkanoic acid are accumulated and converted to PHAs in microorganisms when they are grown under unbalanced nutritional conditions, for example, limiting in nitrogen source or other minimal elements (potassium, iron, sulfur, phosphate and so on), while a carbon source is provided in excess. Polyesters are stored in the microorganisms as an emergency energy source when carbon source from the environment is used up. Stored PHAs can be degraded into carbon dioxide and water by intracellular enzymes therefore generating energy for use.

The physical properties of PHAs are similar to those of petrochemical plastics such as polyethylene. Therefore they can be good alternatives to petrochemical plastics because of their biodegradability. Their production and use will alleviate problems caused by high cost of petroleum and its contribution to pollution. Moreover, the merits of good biocompatibility, biodegradability, and flexibility make PHAs good research candidates for biomedical materials with high values to be applied in bioengineering and biomedical industry.

Over 150 species of microorganisms, including Gram-positive, Gram-negative bacteria from different Genera, and some Archaea were found to produce PHAs.

The general structure of PHAs is shown below. The side chain R can be alkanes with different number of carbon atoms. Different kinds of PHAs are formed with different alkanes. For example, short-chain-length PHAs (scl-PHAs) are composed of monomers containing 3-5 carbon atoms. Poly(3-hydroxybutyrate) [P(3HB) or PHB] in this group contains monomers of 3-hydroxybutyrate (3HB); and Poly(hydroxybutyrate-hydroxyvalerate) (PHBV) is a copolymer comprised of monomers 3HB and 3-hydroxyvalerate (3HV). Medium-chain-length PHA (mcl-PHA) is composed of monomers containing 6-10 carbon atoms.

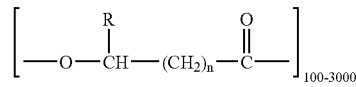

n=1, R=hydrogen, PHAs=poly(3-hyroxypropionate), P(3HP)
R=methyl, PHAs=poly(3-hydroxybutyrate), P(3HB)
R=ethyl, PHAs=poly(3-hydroxyvalerate), P(3HV)
R=propyl, PHAs=poly(3-hydroxycaproate), P(3HC)
R=butyl, PHAs=poly(3-hydroxyheptanoate), P(3HH)
R=pentyl, PHAs=poly(3-hydroxyocatanoate), P(3HO)
R=hexyl, PHAs=poly(3-hydroxynonanoate), P(3HN)
R=heptyl, PHAs=poly(3-hydroxydecanoate), P(3HD)
R=octyl, PHAs=poly(3-hydroxyundecanoate), P(3HUD)
R=nonyl, PHAs=poly(3-hydroxydodecanoate), P(3HDD)
n=2, R=hydrogen, PHAs=poly(4-hydroxybutyrate), P(4HB)
R=methyl, PHAs=poly(4-hydroxyvalerate), P(4HV)
n=3, R=hydrogen, PHAs=poly(5-hydroxyvalerate), P(5HV)

The basic structure of PHAs consists mainly of monomeric units of hydroxyalkanoates (HA). The hydroxyl group of one monomer is attached to the carboxyl group of another by an ester bond to form a long chain type polyester accumulation. The alkyl group (R) in the C-3 or β position of the monomer can be groups of saturated, unsaturated, alcohol or alkanoate with side chain. PHAs are classified according to the type of alkyl group in the β position.

A variety of metabolic pathways and enzymes can synthesize PHAs with different compositions. Different bacteria have different metabolic pathways and enzymes involved in PHA production, which results in the preferential production of a specific type of PHA. Three metabolic pathways for PHA production in microorganisms are found: glycolysis as shown in FIG. 1A, fatty acids degradation as shown in FIG. 1B, and fatty acids biosynthesis as shown in FIG. 1C.

As illustrated in FIG. 1A, acetyl-CoA produced from glycolysis of glucose is converted to acetoacetyl-CoA through catalysis of β-ketothiolase. Acetoacetyl-CoA is reduced by acetoacetyl-CoA reductase to form (R)-3-Hydroxybutyryl-CoA. Short chain length PHAs (scl-PHAs) are produced in the last step through polymerization of PHB polymerase.

As illustrated in FIG. 1B, microorganisms such as *Aeromonas* sp. or *Pseudomonas* sp. use fatty acids as carbon source. Fatty acids can be degraded into short chain fatty acid monomers through β-oxidation and form intermediate products, which include acyl-CoA, enoyl-CoA, (S)-3-hydroxyacyl-CoA, and 3-ketoacyl-CoA. Middle products of enoyl-CoA, (S)-3-hydroxyacyl-CoA, and 3-ketoacyl-CoA which can be catalyzed into (R)-3-hydroxyacyl-CoA through the function of enoyl-CoA hydratase, epimerase and ketoacyl-CoA reductase respectively. In the last step, medium or long chain length PHAs (mcl-PHAs or lcl-PHAs) are formed through the function of PHA synthases (PhaC).

As illustrated in FIG. 1C, different carbon sources could be degraded by microorganisms to yield acetyl-CoA. The acetyl-CoA would not be used to directly produce scl-PHAs but synthesize fatty acids. The intermediate R-3-hydroxyacyl-ACP is converted to R-3-hydroxyacyl-CoA and mcl-PHAs through the catalysis of PhaG (CoA transacylase) and PhaC accordingly.

The important cost factor for the commercialization of microbially-synthesized PHAs is the selection of carbon source for microbial growth substrates. The high cost of traditional culture methods makes PHAs difficult to compete with petrochemical plastics. However, unlike most petrochemical plastics, PHAs is biocompatible and biodegradable. And more than 150 types of PHAs were discovered so far. These properties of PHAs are good for biomedical materials with high values to be applied in bioengineering and biomedical industry. Different PHAs can be produced through different carbon sources or growth substrates accompanied with different strains.

*Bacillus megaterium* belongs to the *Bacillus* sp., which was discovered first to synthesize PHAs and was cultivated in a variety of carbon sources. Attempts at cultivation with different carbon sources were carried out to lower the production cost of PHAs or to produce special PHAs with high values.

The inventor of the invention has discovered a production method for polyhydroxyalkanoates (PHAs) with majority of poly(3-hydroxyvalerate-co-4-hydroxyvalerate) (P3HV-co-P4HV) using succinate as a carbon source after testing several possible carbon sources.

SUMMARY OF THE INVENTION

The objective of the present invention is to provide a production method for PHAs with special composition. This PHAs production method uses succinate as a carbon source and *Bacillus* sp. as the production strain. The PHA products comprise more than 95% poly(3-hydroxyvalerate-co-4-hydroxyvalerate) (P3HV-co-P4HV).

Another object of the invention is to provide a *Bacillus* sp. which could use different carbon sources to synthesize PHAs with different compositions. Besides using succinate as a carbon source, general carbohydrates such as glucose can be the carbon sources for *Bacillus* sp. to produce Poly(3-hydroxybutyrate) (PHB). Different composition of P3HV-co-P4HV could be formed after adjusting the ratio of glucose to succinate in carbon sources. Among them, PHV includes poly(3-hydroxyvalerate) and poly(4-hydroxyvalerate).

PHAs currently synthesized by *Bacillus* sp. belong to the type of scl-PHAs, which include different compositions of P3HB, P(3HB-co-4HB), and P(3HB-co-3HV). As illustrated in FIG. 1A for P3HB synthesis, acetyl-CoA produced from glycolysis of glucose is converted to acetoacetyl-CoA through catalysis of β-ketothiolase, followed by reduction through acetoacetyl-CoA reductase to form (R)-3-Hydroxybutyryl-CoA. Finally, short chain length P3HB is produced through polymerization of PHB polymerase. The mechanisms for P4HB, P3HV and P4HV synthesis are not clear at present. It's possible that Gram-positive bacteria such as *B. megaterium* could synthesize P4HB and p3HV linked with P3HB. The possible synthetic pathway for P3HV is described below. First, acetyl-CoA enters TCA cycle to yield succinyl-CoA, followed by conversion to form propionyl-CoA. Formation of 3-ketovalery-CoA through condensation of propionyl-CoA and acetyl-CoA is followed by reduction to yield (R)-3-Hydroxyvaleryl-CoA. Final copolymer P(3HB-co-3HV) is formed through catalysis of PhaC. Production of P4HB occurs via conversion of succinyl-CoA to succinate semialdehyde, then to 4-hydroxybutyrate (4HB). 4HB could be converted to 4-hydroxybutyryl-CoA as the precursor for PHAs. Polymers containing P4HB is formed by polymerization through PhaC after P4HB is linked to PHA particles. Practically, propionate is used as carbon source to increase the content of 3HV comprising in PHAs in some special studies only.

The present invention provides a method to let microorganisms produce PHAs containing mainly P3HV-co-P4HV units.

To fulfill the abovementioned objectives, the invention uses succinates and its derivatives as carbon source.

The microorganisms used to fulfill the abovementioned objective are Gram-positive bacteria grown with succinate such as *Bacillus* sp. The representative strains of *Bacillus* sp. in this study are *B. megaterium* and several other microorganisms isolated from *Bacillus* sp. strains.

The culture medium is based on M9 medium containing carbon sources according to the needs of the experiments.

The basic culture medium M9 contains trace elements required for growth of microorganisms and phosphate. Other carbon sources are supplemented as needed.

DETAILED DESCRIPTION OF THE PREFERRED EMBODIMENT

EXAMPLE

Figure 1A:
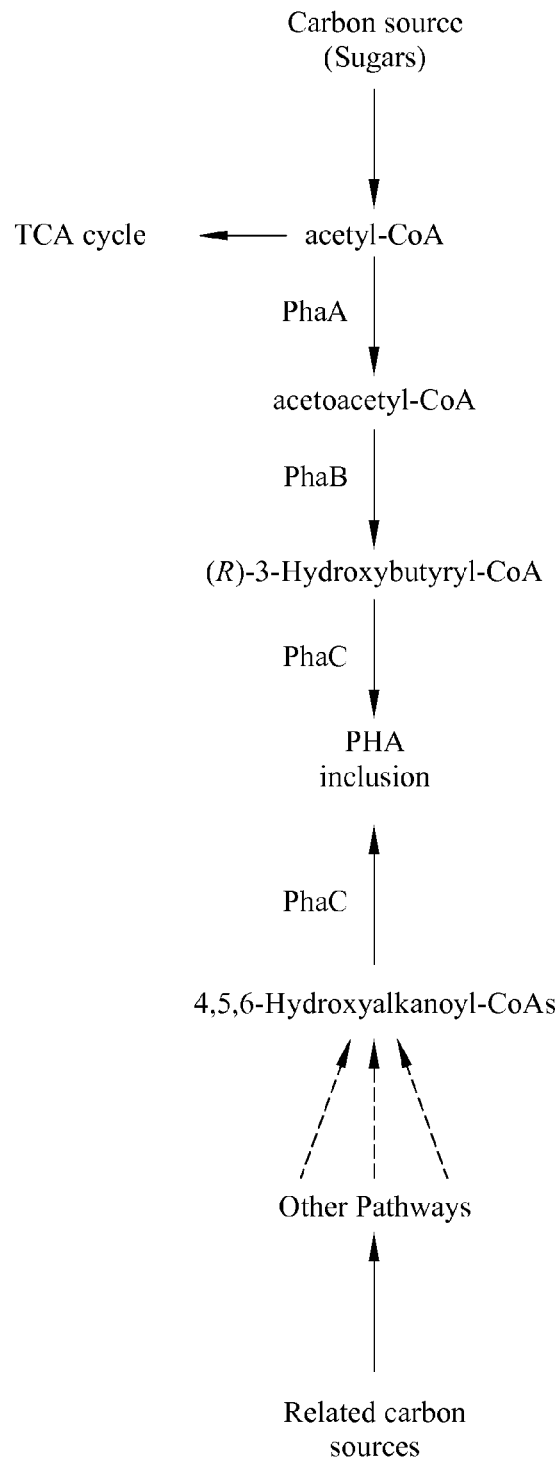
FIG. 1A illustrates the diagram of metabolic pathways for PHAs production in glycolysis.
Figure 1B:
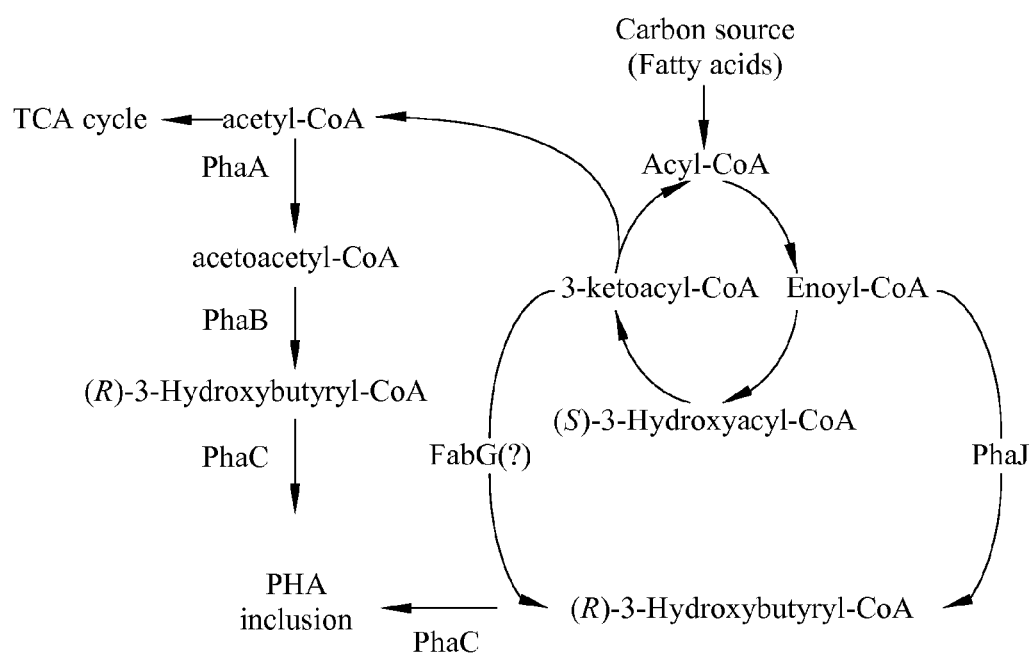
FIG. 1B illustrates the diagram of metabolic pathways for PHAs production in fatty acids degradation.
Figure 1C:
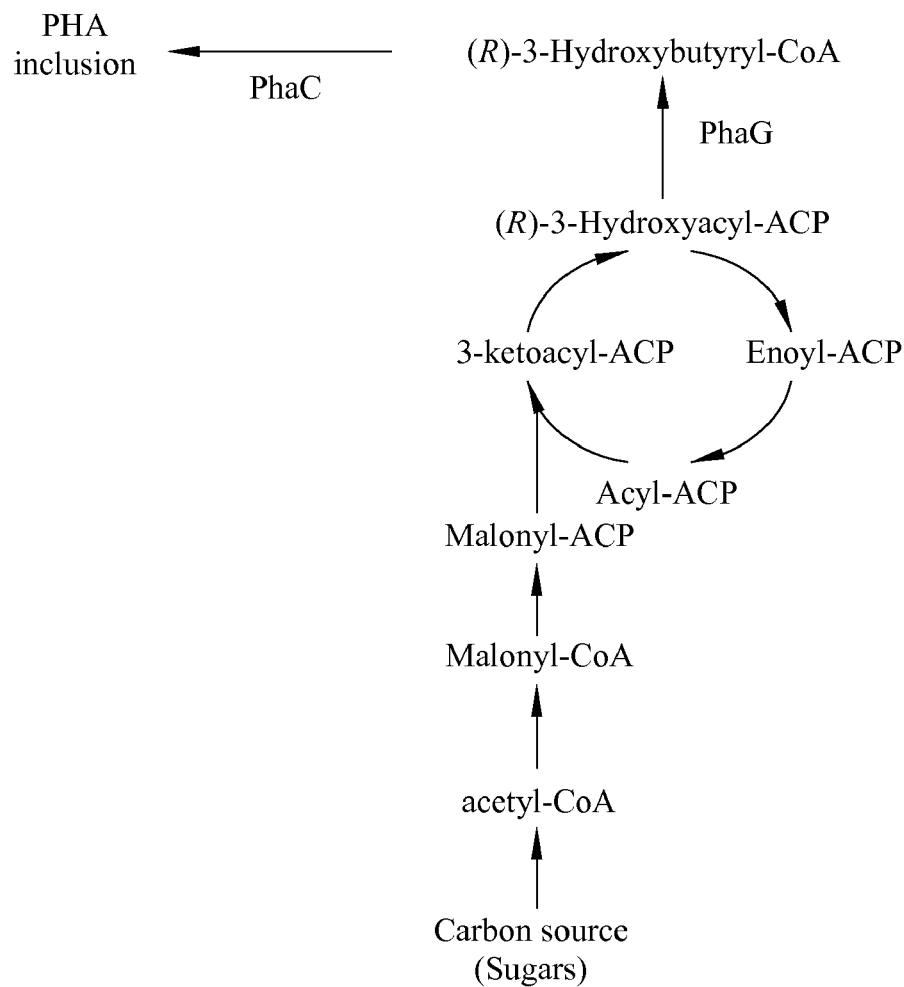
FIG. 1C illustrates the diagram of metabolic pathways for PHAs production in fatty acids biosynthesis.

Different PHAs Produced by *Bacillus* sp. with Various Carbon Sources and the Analysis of PHAs Bacteria synthesize PHAs in various structures and compositions when supplemented with different carbon sources through different metabolic pathways. The known PHAs synthetic pathways of *Bacillus* sp. are based on PHB and PHV produced through glycolysis. The present invention attempts to synthesize PHAs in various forms such as PHB, PHB-co-PHV, and PHV through different carbon sources for *Bacillus* sp. The PHAs were extracted from bacteria with the chloroform-sodium hypochlorite extraction method after cultivation. This is followed by gas chromatographic (GC) analysis to assay the composition of PHAs accumulated in bacteria.

Cultivation of Bacteria

The culture medium is based on M9 medium (5× minimal salt medium: 33.9 g/L $NaHPO_4$, 15 g/L $KH_2PO_4$, 2.5 g/L NaCl, 5 g/L $NH_4Cl$) with 4% of different carbon sources including glucose, succinate, sucrose, glycerol and organic acids such as decanoic acid, caprylic acid, etc. *Bacillus megaterium* and KC046, KC056 isolated from *Bacillus* sp. were cultivated in incubator at 30° C. with shaking at 150 rpm for 48 hours.

Chloroform-Sodium Hypochlorite Extraction Method

Bacterial pellets were resuspended in 10 ml of 4.8% sodium hypochlorite solution. The mixture was added with 10 ml of chloroform and agitated at 150 rpm at 55° C. for 3 hours. The phases were separated after centrifugation at 12000×g for 20 min. The organic layer was collected and added with 200 ml of 95% ice-cold alcohol to precipitate PHAs. After another centrifugation at 12000×g for 30 min, the supernatant was removed and the pellet was washed with sterile water several times. The pellet was dried at 105° C. oven to yield white powder of PHAs.

GC Analysis of Bacteria Composition

Cells of *Bacillus* sp. including *Bacillus megaterium* and *Bacillus* sp. KC046, KC056 after 48 hours cultivation were harvested. 20 mg of purified PHAs or 30 mg of dried cell pellets were added with 2 ml of 1% $H_2SO_4$/methanol and 2 ml of chloroform, sealed and reacted at 105° C. for at least 6 hours. 40 μl of internal label material was weighed and added after the reaction was completed. 1 ml of 1N NaCl was added and mixed gently. The solution was stayed for 30 min for phase separation. The lower layer was subjected for analysis. 2 μl of the sample was aliquoted and injected into GC for analysis.

The GC analysis was performed in the following condition: 17 ml/min carrier gas, 250° C. injector temperature, and 250° C. detector temperature. The GC oven program began at 75° C., then 25° C./min to 200° C. with a total separation time of 10 min. The process of gas chromatography is carried out in a GC instrument (Termo electron S.p.A Strada Rivoltana) equipped with a flame ionization detector (FID) detector and a 30 m×0.53 mm i.d. Stabilwax capillary column (Crossbond Carbowax-PEG).

Nuclear Magnetic Resonance (NMR) Analysis of PHA Product 3 mg of PHAs powder was dissolved in 0.5 ml D-chloroform and dried at 40° C. oven for 3 hours. The solution was put into an NMR assay tube for National Tsing-Hua University to carry out NMR analysis.

Analysis of PHB and PHB-co-PHV Standards

Figure 2A:
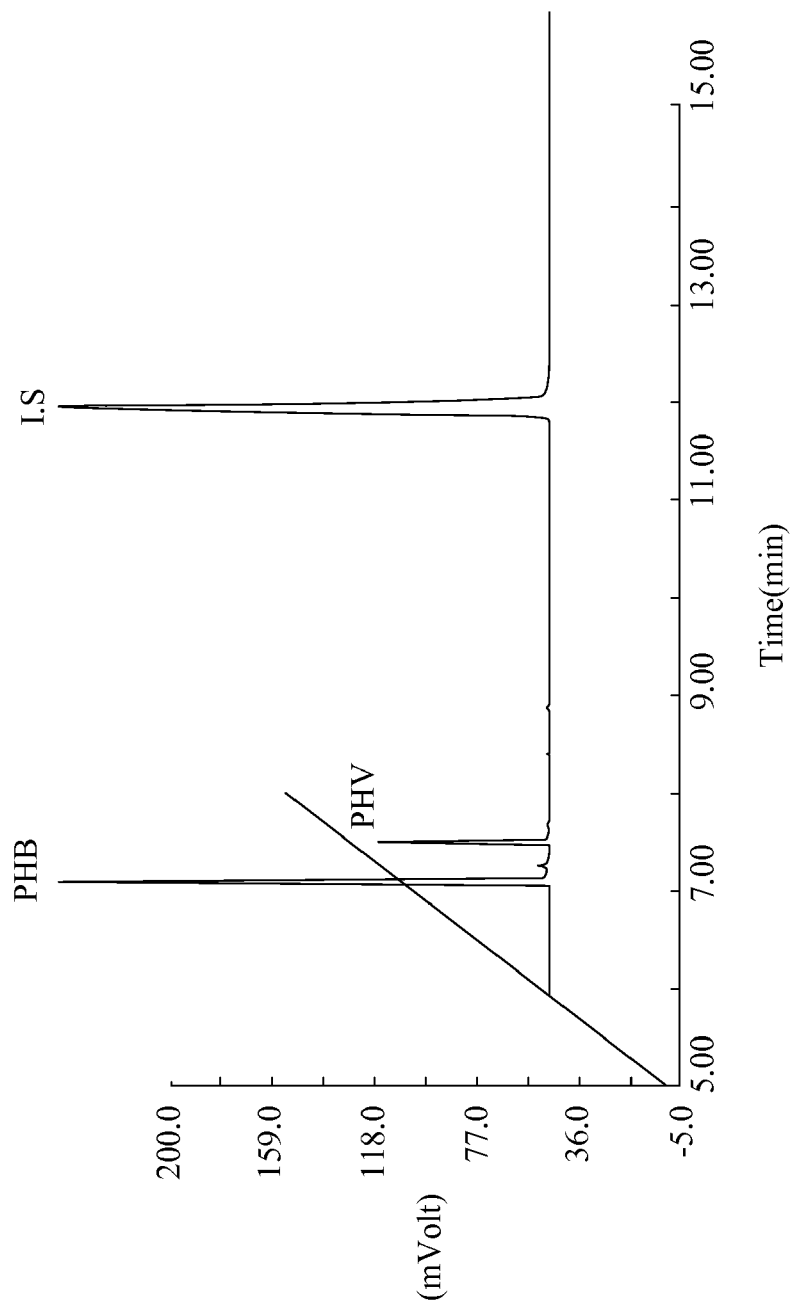
FIG. 2A illustrates the diagram of GC analysis for the PHAs production in PHB-co-PHV standard.
Figure 2B:
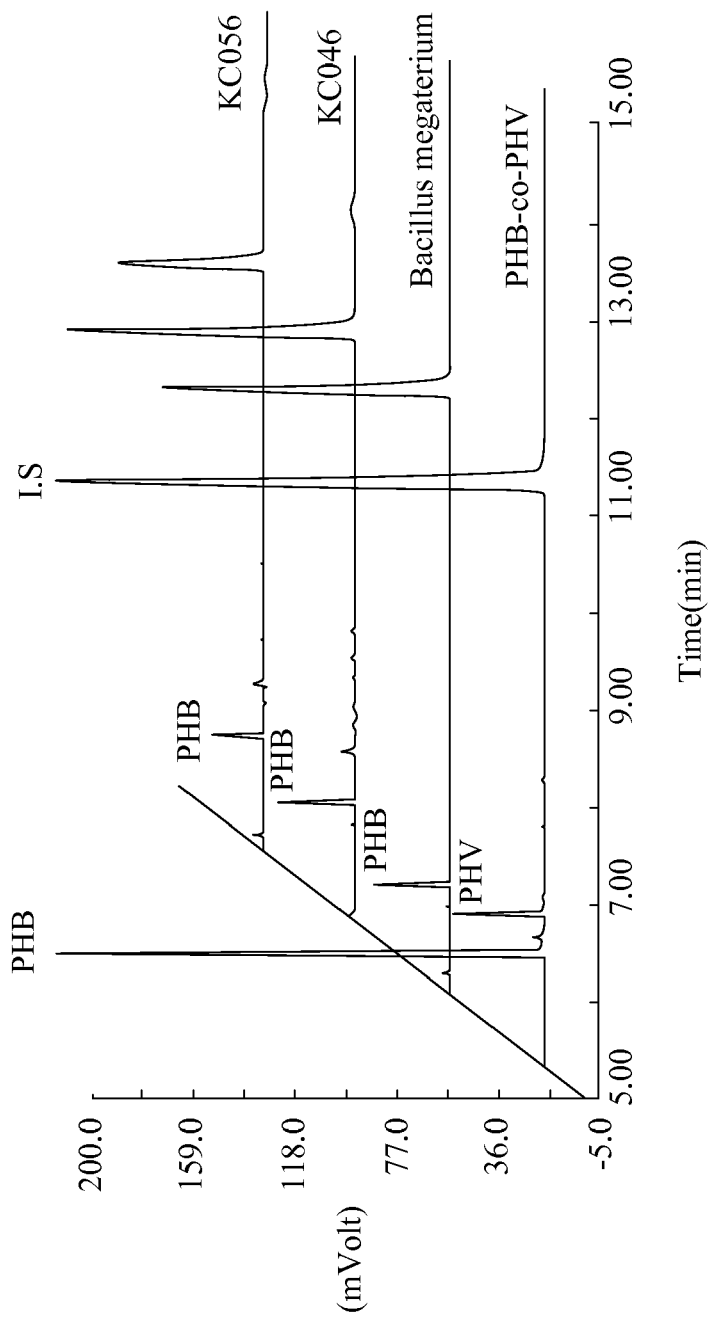
FIG. 2B illustrates the diagram of GC analysis for the PHAs production with *Bacillus megaterium* and *Bacillus* sp. using glucose or sucrose as the carbon source.
Figure 2C:
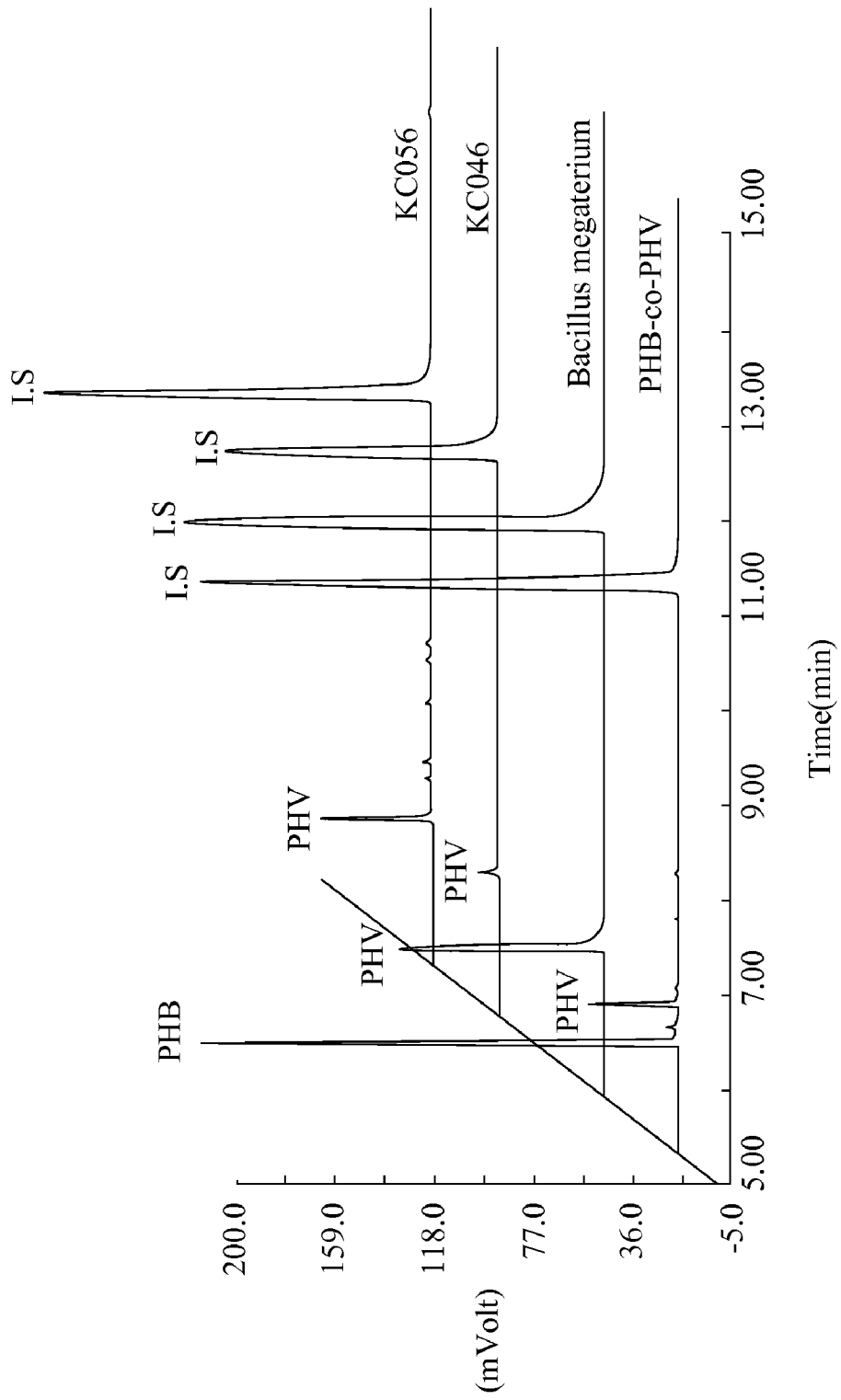
FIG. 2C illustrates the diagram of GC analysis for the PHAs production with *Bacillus megaterium* and *Bacillus* sp. using succinate as the carbon source.

Referred to FIGS. 2A-2C. FIG. 2A is the GC analysis of PHB-co-PHV standard. The PHB absorption peak was present at a retention time of 6.1 min, and that for PHV was at 6.7 min I.S. equals to internal standard. First, the P3HB standard and 3.9% PHB-co-PHV standard was analyzed by GC as control group. FIG. 2A showed the analysis result of standards. PHB standard was hydrolyzed to hydroxybutyrate (HB) monomers at 100° C. for 4 hours after addition of chloroform and acidic methanol. HB monomers were precipitated with 1N NaCl and analyzed with GC. The retention time of HB monomer was at 6.1 min. Two peaks at 6.1 min and 6.7 min were shown when the same hydrolysis process was carried out with the PHB-co-PHV standard. Therefore, the retention time for the HV monomers obtained from hydrolyzed PHV was postulated to be at 6.7 min, and that of the diphenyl ether served as an internal standard was at 11 min. The samples and the PHAs accumulated in *Bacillus* sp. could be analyzed and compared with standards when all the retention times were obtained.

Supplementation of Succinate during Cultivation of *Bacillus* sp. to Yield High Purity PHV Analysis of PHAs obtained from *Bacillus* sp. using glucose or sucrose as the carbon source showed peak signals at 6.1 min shown in FIG. 2B. This indicated that the composition of accumulated PHAs in *Bacillus* sp. is mostly PHB.

As illustrated in FIG. 2B, PHAs accumulated in *Bacillus megaterium* and *Bacillus* sp. KC046, KC056, which used glucose as the carbon source, were analyzed with GC. The retention times of absorption peaks for HB is at 6.1 min, HV at 6.7 min and the internal standard is at 11 min. It showed that hydrolyzed products of PHAs from *Bacillus* sp. were mostly HB monomers when glucose was supplemented as the carbon source. PHB was the major product.

PHAs accumulated in *Bacillus megaterium* and *Bacillus* sp. KC046, KC056 were analyzed after extraction as described above when succinate was supplemented as the sole carbon source. The retention time of the major peak was shown at 6.7 min, which is the same as that of HV monomer. Signal was very weak at 6.1 min, which is the signal position for HB monomers. FIG. 2C showed that more than 95% of the PHAs accumulated in *Bacillus* sp. were PHV when succinate was supplemented as the sole carbon source. The content of PHB was too low to be assayed with GC.

As illustrated in FIG. 2C, PHAs accumulated in *Bacillus megaterium* and *Bacillus* sp. KC046, KC056, which used succinate as the carbon source, were analyzed with GC. The retention times of absorption peaks for HB is at 6.1 min, HV at 6.7 min and the internal standard is at 11 min. It showed that hydrolyzed products of PHAs from *Bacillus* sp. were mostly HV monomers when succinate was supplemented as the carbon source. PHV was the major product.

PHV Accumulated in *Bacillus* sp. with Succinate as the Carbon Source was P(3HV-co-4HV) through NMR Analysis To further analyze the chemical structures of PHAs accumulated in *Bacillus* sp. (KC046 and KC056) with succinate as the carbon source, NMR analysis was used. Dry cell pellets of *Bacillus* sp. KC046 and KC056 after cultivated in M9 media with succinate as the carbon source were sent to National Tsing-Hua University to carry out NMR analysis and compared with the published NMR profile of P(3HV-co-4HV). The results from *Bacillus* sp. KC046 and KC056 were identical. PHAs accumulated in *Bacillus* sp. KC046 and KC056 were P(3HV-co-4HV) copolymer. The ratio of 3HV and 4HV was 1:2 after the signal intensity of $^3$H-NMR was analyzed.

Two-Stage Cultivation Process

The invention also performed the two-stage cultivation process since *Bacillus* sp. could be cultivated with several inexpensive carbon sources. First, an inexpensive carbon source such as glucose and plenty of nitrogen sources were provided to enhance the growth of each bacterium strain within short time of cultivation. The M9 media containing 4% succinate was replaced when the cell growth reached plateau. PHVs accumulated in cells were harvested after 24 hours. The biomass level could increase to 300% with the yield of PHV increased in direct proportion. The purities of PHV were exceeding 95% after GC analysis.

The invention is a method providing high purity PHV with succinate as a growth substrate (carbon source). The merits of the present invention, when compared with other known technology, can be summarized as the following:

(1) The invention is a very inexpensive method so far to produce PHV. The purity of PHV is the highest too. No further purification steps is needed for high purity (>95%) PHV.

(2) The microorganism used in this invention is *Bacillus* sp., which is relatively easy to culture. The costs for culture and manipulation are relatively low.

(3) *Bacillus* sp. used in this invention can be cultivated with different substrate or combined substrates to synthesize PHB-co-PHV. The ratio and composition can be easily adjusted to fit into various applications.

(4) At present, most of the PHA-producing bacteria are Gram-negative and as a result, frequent contamination of Lipopolysaccharides (LPS) occurs during the purification process. LPS is an endotoxin, which can induce allergic responses easily. PHAs purified from Gram-negative bacteria for bioplastic production and eventual use in medical settings is risky because of the possible contamination of endotoxins. *Bacillus* sp. used in this invention is Gram-positive, no LPS residue will be found during PHAs extraction. Therefore PHAs produced in the invention are suitable to be used for medical materials, further increasing its value.

The present invention disclosed above should not be limited by any of the above-described exemplary embodiments. These examples should not, however, be considered to limit the scope of the invention, it is contemplated that modifications will readily occur to those skilled in the art, which modifications will be within the spirit of the invention and the scope of the appended claims.

What is claimed is:

1. A method of producing a high purity polyhydroxyvalerate (PHV), comprising the step of cultivating microorganisms using succinate as a carbon source to produce PHV wherein the microorganism is *Bacillus* sp and wherein the purity of the PHV is more than 95%.

2. The method as claimed in claim 1, wherein the PHV is comprised of poly(3-hydroxyvalerate-co-4-hydroxyvalerate) (P3HV-co-P4HV).

3. The method as claimed in claim 1, wherein the microorganism is cultivated in M9 base medium, or basic medium containing trace elements and phosphate salts.

* * * * *